United States Patent [19]

Furutachi et al.

[11] 4,021,428

[45] May 3, 1977

[54] 4-PIPERIDINO-5-OXO-2-PYRAZOLINES

[75] Inventors: Nobuo Furutachi; Atsuaki Arai, both of Minami-ashigara, Japan

[73] Assignee: Fuji Photo Film Co., Ltd., Minami-ashigara, Japan

[22] Filed: Aug. 22, 1975

[21] Appl. No.: 607,740

Related U.S. Application Data

[63] Continuation of Ser. No. 455,094, March 27, 1974, abandoned.

[30] Foreign Application Priority Data

Mar. 27, 1973 Japan .............................. 48-35378

[52] U.S. Cl. ........................ 260/293.7; 260/293.62; 260/293.67; 260/293.68; 260/310 A; 260/295 R; 260/294.8 D; 260/294.8 R; 260/295 E; 260/296 R; 96/56.5; 96/100; 260/283 SA; 260/283 S; 260/289 R; 260/288 R; 260/287 R; 260/283 R

[51] Int. Cl.[2] ........................................ C07D 401/04

[58] Field of Search ........ 260/293.7, 283 R, 283 S, 260/283 SA, 287 R, 288 R, 289 R

[56] References Cited

UNITED STATES PATENTS

| | | | |
|---|---|---|---|
| 2,506,654 | 5/1950 | Stein et al. | 260/293.7 |
| 3,320,253 | 5/1967 | Muhle | 260/293.7 |
| 3,519,429 | 7/1970 | Lestina | 260/310 A |

OTHER PUBLICATIONS

Heterocycle Compounds, ed. Elderfield (1950), vol. 1, pp. 631–634.
C.A. 58: 7921(b), (1963), Kurihara et al.

*Primary Examiner*—Henry R. Jiles
*Assistant Examiner*—Robert T. Bond
*Attorney, Agent, or Firm*—Sughrue, Rothwell, Mion, Zinn & Macpeak

[57] ABSTRACT

4-Piperidino-5-oxo-2-pyrazoline represented by the following general formula (X);

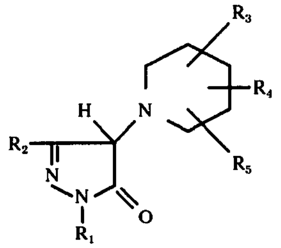

(X)

wherein $R_1$ represents a group having about 6 to about 40 carbon atoms, $R_2$ represents a hydrogen atom or a group having 0 to about 45 carbon atoms, $R_3$, $R_4$ and $R_5$ each represents a hydrogen atom or a group having 0 to 20 carbon atoms, and $R_3$ and $R_4$ may combine to form an aliphatic ring, an aromatic ring or a heterocyclic ring. The 4-piperidino-5-oxo-pyrazolines are useful as magenta color couplers.

8 Claims, No Drawings

4-PIPERIDINO-5-OXO-2-PYRAZOLINES

This application is a continuation of Ser. No. 455,094, filed Mar. 27, 1974, now abandoned.

BACKGROUND OF THE INVENTION

1. Field of the Invention

The present invention relates to 5-oxo-2-pyrazolines and to a process for producing same. More particularly, it relates to 1,3,4-Trisubstituted-5-oxopyrazolines substituted with a piperidino 0 in the 4-position and a process for producing same. 3,006,759.

In particular, a characteristic aspect of the present invention is to produce 5-oxo-2-pyrazolines by reducing 5-oxo-2-pyrazoline 4-pyridinium salt derivatives.

2. Description of the Prior Art

It is well known that 1,3-di-substituted-5-oxo-2-pyrazolines are important compounds as magenta couplers for color photographic light-sensitive materials utilizing the color subtractive process and are useful as intermediates for many medicines and dyes. For example, when an exposed conventional color photographic light-sensitive material having a silver halide emulsion containing a 1,3-di-substituted-5-oxo-2-pyrazoline is subjected to color development-processing, the color coupler oxidatively couples with the oxidized p-phenylenediamine color developing agent to form a corresponding azomethine dye.

It is well known that four equivalents of silver halide are theoretically necessary as an oxidizing agent in order to form one molecule of an azomethine dye through the color coupling reaction of such a 1,3-di-substituted-5-oxo-2-pyrazoline coupler. In contrast, 1,3,4-trisubstituted-5-oxo-2-pyrazolines containing in the 4-position a substituent which can be eliminated easily after the coupling reaction with an oxidized color developing agent theoretically require only two equivalents of silver halide to form the dye.

For this reason, 5-oxo-2-pyrazolines having an eliminatable substituent in the 4-position are extremely important compounds in the production of color photographic light-sensitive materials.

SUMMARY OF THE INVENTION

An object of the present invention is to provide 1,3,4-trisubstituted-5-oxo-2-pyrazolines containing a piperidino group, a substituted piperidino group or a ring-fused piperidino group in the 4-position and to provide a process for producing these compounds in high purity and in high yield using a simple procedure.

As a result of extensive investigations, the inventors have successfully found novel 4-piperidino-5-oxo-2-pyrazolines and a process for producing same by catalytically reducing a 5-oxo-2-pyrazoline 4-pyridinium salt using a metal catalyst, thus conveniently attaining the above-described object.

The 4-piperidino-5-oxo-2-pyrazolines of the present invention include compounds represented by the following general formula (X);

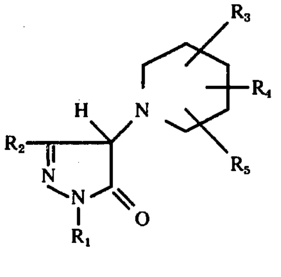

(X)

wherein $R_1$ represents a group having about 6 to about 40 carbon atoms, $R_2$ represents a hydrogen atom or a group having 0 to about 45 carbon atoms, $R_3$, $R_4$ and $R_5$ each represents a hydrogen atom or a group having 0 to 20 carbon atoms, or $R_3$ and $R_4$ may combine to form an aliphatic ring, an aromatic ring or a heterocyclic ring.

It has now been demonstrated that 4-piperidino- and 4-substituted piperidino-5-oxo-pyrazolines obtained by the present invention are extremely useful compounds having the above-described 2-equivalent characteristics, and are usable as a magenta coupler in a broad range of types of color photographic light-sensitive materials.

DETAILED DESCRIPTION OF THE INVENTION

Heretofore, several 5-oxo-2-pyrazolines having a substituent in the 4-position are known. However, 1,3,4-trisubstituted-5-oxo-2-pyrazolines containing a piperidino group, a substituted piperidino group or a ring-fused piperidine group in the 4-position, as obtained by the present invention, are novel compounds not described in any prior art patents and literature.

More specifically, $R_1$ can be a phenyl group or a substituted phenyl group having one or more substituents, e.g., substituents such as an alkyl, alkoxy, aryl, aryloxy, alkoxycarbonyl, acylamino, carbamoyl, sulfo, alkylsulfamido, arylsulfamido, sulfamoyl, or carboxy group, etc., or a halogen atom.

$R_2$, more specifically, can be a non-carbon containing substituent, e.g., a hydroxy, amino, or sulfo group, etc., or a halogen atom, or a substituent having 1 to 45 carbon atoms, e.g., an alkyl, aryl, alkoxy, aryloxy, carboxy, alkoxycarbonyl, alkylamino, cycloalkylamino, dialkylamino, diarylamino, arylamino, acylamino, carbamoyl, N-alkylacylamino, N-arylacylamino group, etc., or a ureido group or a substituted ureido group, e.g., an N-alkylureido, N-arylureido, N-cycloalkylureido group, etc., or a diacylamino group.

Suitable examples of $R_3$, $R_4$, and $R_5$ are non-carbon atom group having 0 carbon atom, e.g., containing substituents such as a halogen atom, an amino, hydroxy or sulfo group, or a group having 1 to about 20 carbon atoms, e.g., an alkyl, aralkyl, alkoxy, aryloxy, acylamino, alkylsulfamido, anylsulfamido, amido, alkylamino or arylamino group, etc., $R_3$ and $R_4$ can also combine to form a fused ring, an alicyclic ring having 3 to 8 carbon atoms, e.g., cyclopentane, cyclohexane, cycloheptane, etc.; a benzene ring; a substituted benzene ring substituted with a halogen atom, an amino, hydroxy, alkyl, alkoxy, acylamino, sulfo, carboxy, alkylsulfonamido, amido, arylsulfonamido, alkylamino, arylamino group, etc.; or a heterocyclic ring comprising a carbon atom and at least one hetero atom selected from a nitrogen, sulfur and oxygen atom, e.g., a pyridine, tetrahydrofuran, tetrahydrothiophene, thiophene ring, etc.

While the above exemplifies $R_1$, $R_2$, $R_3$, $R_4$ and $R_5$, the substituents present are not overly of concern and any known substituents present in known 4-equivalent pyrazolone couplers can be selected and suitably employed.

The 5-oxo-2-pyrazoline 4-pyridinium salts IV/V used as a starting material in this invention are also novel compounds not described in any prior art patents or literature. The inventors have found that they can be prepared using either of the following two processes.

That is, one process comprises halogenating a 1,3-di-substituted-5-oxo-2-pyrazoline represented by the following general formula (I);

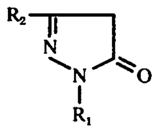
(I)

wherein $R_1$ represents a group having about 6 to about 40 carbon atoms, and $R_2$ represents a hydrogen atom or a group having 0 to about 45 carbon atoms, according to, e.g., U.S. Pat. No. 3,006,759. The 1,3-di-substituted 5-oxo-2-pyrazoline compounds represented by the general formula (I) used as a starting material can be prepared using synthetic techniques analogous to those described in U.S. Pat. Nos. 3,337,344, 2,127,269 and 3,558,319. Suitable halogenating agents are halogens such as $Cl_2$, $Br_2$ and $I_2$, sulfanyl chloride, N-chlorosuccinimide, N-bromosuccinimide, N-iodosuccinimide, N-chlorobenzotriazole, etc. Suitably the halogenating agents are used in an equimolar amount to the compound of the general formula (I), since the reaction is best controlled. An equivalent amount of the halogenating agent in excess of 1 mole is not preferred since undesired positions are halogenated. Generally, reaction temperatures in this step can range from about −10° to 50° C, preferably, 0° to 20° C. The reaction is generally conducted in a solvent. Suitable solvents are protic solvents such as carboxylic acid-type solvents e.g., acetic acid and aprotic solvents there can also such as non-poler solvents, e.g., chloroform, carbon tetrachloride, methylene chloride, tetrahydrofuran, dioxane etc. The amount of the solvents to be employed is generally about 10% by volume per weight of the compound of the general formula (I). After the reaction has been completed, the solvent is evaporated to dryness. The thus obtained 1,3-di-substituted-4-halogeno-5-oxo-2-pyrazoline (II) is sufficiently pure to be used, but if desired it can be recrystallized from suitable solvents. Where acetic acid is used as a solvent, the reaction mixture can be poured into ice-water and then filtered. The solid product is dried and recrystallized for recovery.

The resulting 1,3-di-substituted-4-halogeno-5-oxo-2-pyrazoline prepared as described above and represented by the following general formula (II);

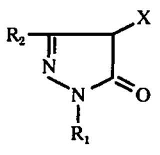
(II)

wherein $R_1$ and $R_2$ are the same as defined above, and X represents a chlorine atom, a bromine atom or an iodine atom, is then reacted with an N-heteroaromatic compound represented by the following general formula (III);

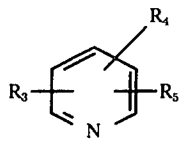
(III)

wherein $R_3$, $R_4$ and $R_5$ each represents a hydrogen atom or a group having 0 to 20 carbon atoms, or $R_3$ and $R_4$ may combine to form an aliphatic ring, an aromatic ring or a heterocyclic ring.

The compounds of the general formula (III) are known and are generally commercially available. In this step of the synthesis a suitable molar ratio of the compound of the general formula (II) to the compound of the general formula (III) can suitably range from about ½ to 1/20, by weight, preferably ¼ to 1/10. Suitable temperature ranges for conducting this step of the synthesis are of from about 10° to 100° C, preferably 20° to 60° C. The reaction can be conducted in the absence of a solvent since the compound of the general formula (III) per se acts as a solvent. In such a case the compound of the general formula (III) is used in an amount of about 5 to 50% by weight to the total weight of the reactants (II + III). However, solvents, e.g., alcohols such as methanol or ethanol, benzene, acetonitrile, chloroform, etc., can, of course, be effectively used. In this case the solvent is suitably employed in an amount of from about 20 to 500 ml per 10 g of the compound of the general formula (II). When the reaction of this step is conducted in the absence of a solvent, the product is extracted from the reaction mixture using a suitable solvent such as diethyl ether, ethyl acetate, chloroform, etc., washed with water, dried and recrystallized. Where the reaction is conducted using a solvent, the solvent is evaporated. After extracting with a suitable solvent such as diethyl ether, ethyl acetate, chloroform, etc., the extract is dried over sodium sulfate. The solvent is evaporated off to obtain the product, which can be recrystallized, if desired.

Another process comprises heating a 5-oxo-2-pyrazoline represented by the general formula (I) and an N-heteroaromatic compound represented by the general formula (III) in the presence of an equimolar amount of iodine to accomplish the reaction. This reaction can be conducted in the presence of a solvent, e.g., alcohols such as methanol, ethanol, etc., acetonitrile, chloroform, benzene, or the like. The solvent is generally used in an amount of about 20 to about 500 ml, preferably 50 to 100 ml, to about 10 g of the compound of the general formula (I). The reaction temperatures generally range from about 20° to about 200° C, preferably while heating to reflux on a steam bath.

Of these two processes, the former process provides a good yield and is particularly useful for producing widely usable 5-oxo-2-pyrazoline 4-N-heteroaromatic ylides. According to this process, the 4-halogeno-5-oxo-2-pyrazoline, obtained from the 5-oxo-2-pyrazoline, need not be isolated in a pure state. That is, when a desired N-heteroaromatic compound is reacted with the crude 4-halogenated product under heating, ylides can be isolated at this stage with ease as yellow crystals without any losses, since the resulting 5-oxo-2-pyrazoline 4-N-heteroaromatic ylides possess an extremely low solubility.

The ylide products obtained under usual conditions are obtained as an inner salt (an N-heteroaroamtic ylide type) represented by the following general formula (IVa) or (IVb);

(IVa)

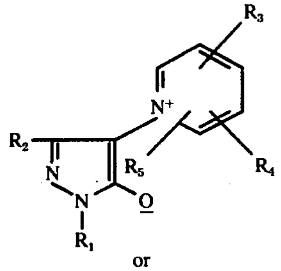

or (IVb)

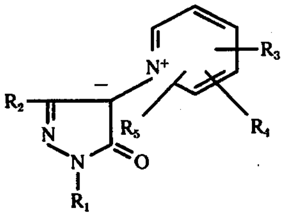

wherein $R_1$, $R_2$, $R_3$, $R_4$ *and* $R5$ are the same as defined above. The above compounds of the general formulas (IVa) and (IVb) are tautomeric forms. However, in some cases, a corresponding hydrogen halide salt thereof represented by the following general formula (V);

(V)

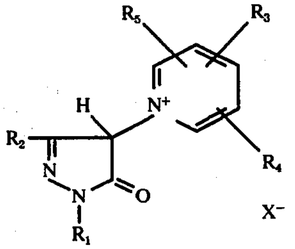

wherein $R_1$, $R_2$, $R_3$, $R_4$, $R_5$ and X are the same as defined above, is present in the product in a small amount. Where X is chlorine, bromine or iodine, the corresponding hydrogen halide salt exists. Other salts can also be suitably employed, e.g., the perchlorate, periodate or p-toluene sulfonate salt and are prepared by anion conversion using an excess of a perhalic acid or a silver salt of a perhalic acid. However, the presence this compound is not at all inconvenient in the present invention.

The 5-oxo-2-pyrazoline 4-pyridinium derivatives of the present invention include the compounds represented by the above-described general formulae (IVa), (IVb) and (V). These compounds individually or in admixture are reduced to the compounds of the general formula (X).

The compounds, represented by the above-described general formulae (I) and (III), to be used in the present invention are described in detail below.

As the 5-oxo-2-pyrazolines represented by the general formula (I), those compounds which are conventionally used as a 4-equivalent magenta coupler in the photographic field can be used regardless of the total of the number of carbon atoms of the substituents in both the 1-position and the 3-position of the pyrazoline ring. The reaction site is located at the 4-position of the 5-oxo-2-pyrazoline and the substituents which are in the 1- and 3-positions do not possess a particularly important significance from the standpoint of the synthesis.

Preferable examples of $R_1$ include groups having about 6 to about 40 carbon atoms (e.g., a phenyl group or a phenyl group having one or more substituent groups such as an alkyl group (e.g., having 1 to 30 carbon atoms), an alkoxy group (e.g., having 1 to 30 carbon atoms), an aryl group (e.g., phenyl, naphthyl, etc.), an aryloxy group (e.g., phenoxy, naphthoxy, or a phenoxy or naphthoxy substituted with a group having 1 to 10 carbon atoms), a halogen atom, an alkoxycarbonyl group (e.g., having 1 to 30 carbon atoms), an acylamino group (e.g., having 1 to 30 carbon atoms), a carbamoyl group (e.g., having 1 to 30 carbon atoms), a sulfo sulfo group, an alkylsulfonamido group (e.g., having 1 to 30 carbon atoms), an arylsulfonamido group (e.g., phenylsulfonamido, naphthylsulfonamido, or phenyl- or naphthyl-sulfonamido having a substituent containing 1 to 20 carbon atoms), a sulfamoyl group (e.g., having 1 to 30 carbon atoms), and a carboxy group, etc.).

Preferable examples of $R_2$ include a hydrogen atom, a halogen atom, or a group having O (e.g., an amino group, a hydroxy group, a sulfo group, etc. ) to about 45 carbon atoms (e.g., a group having 1 to 45 carbon atoms), more specifically an alkyl group (e.g., having 1 to 45 carbon atoms), an aryl group (e.g., phenyl, naphthyl or substituted phenyl or substituted naphthyl substituted with a substituent containing 1 to 30 carbon atoms), an alkoxy group (e.g., having 1 to 45 carbon atoms), an aryloxy group, an alkoxycarbonyl group (e.g., having 1 to 40 carbon atoms), an alkylamino group (e.g., having 1 to 45 carbon atoms), a cycloalkylamino group (e.g., having 3 to 8 carbon atoms such as cyclopenthylamino, cyclohexylamino, cycloheptylamino, and cycloalkylamino having a substituent group containing 1 to 30 carbon atoms), a dialkylamino group (e.g., in which the alkyl moiety has 1 to 20 carbon atoms), a diarylamino group (e.g., diphenylamino, dinaphthylamino, substituted diphenylamino and substituted dinaphthylamino having a substituent containing 1 to 15 carbon atoms), an arylamino group (e.g., an amino group containing an aryl substituent having 6 to 45 carbon atoms, e.g., anilino), an acylamino group (e.g., an amino group containing an acyl substituent having 1 to 45 carbon atoms), an N-alkylacylamino group (e.g., an N-alkylacylamino group in which the acyl moiety has 1 to 30 carbon atoms and the alkyl moiety has 1 to 10 carbon atoms), a carbamoyl group (e.g., having 1 to 45 carbon atoms), an N-arylacylamino group, (e.g., a phenylacylamino, a naphthylacylamino, a substituted phenylacylamino group containing a phenyl substituent having 1 to 10 carbon atoms, in which the acyl moiety has 1 to 20 carbon atoms), a ureido group (e.g., ureido, N-alkylureido, N-phenylureido, N-naphthyl ureido having 1 to 45 carbon atoms and N-substituted phenyl ureido, N-substituted naphthyl ureido having 1 to 20 carbons in the substituent group, and N-cycloalkyl ureido having 5 to 30 carbon atoms), a diacyl amino group (e.g., a diacylamino group having 1 to 20 carbon atoms in each acyl substituent), etc.

Specific 4-equivalent couplers represented by the general formula (I) are those couplers illustrated, e.g., in U.S. Pat. Nos. 2,600,788, 3,062,653, 3,337,344, 2,127,269, 3,558,319, etc.

As the pyridine ring-containing compounds represented by the general formula (III), any compounds which are capable of reacting with a 4-halo-5-oxo-2-pyrazoline to form a pyridinium salt (ylide compound) can be used as the starting material in the present invention. Since the reaction site is located at the nitrogen atom of the pyridine ring, $R_3$, $R_4$ and $R_5$ are not particularly limited.

Preferable examples of the compounds of the general formula (III) are those compounds wherein $R_3$, $R_4$ and $R_5$ each represents, e.g., a hydrogen atom, a hydroxy group, a halogen atom, an amino group, an amide group, a sulfo group and a group containing 1 to 20 carbon atoms and more specifically an alkyl group (e.g., containing 1 to 20 carbon atoms), an aralkyl group (e.g., containing 1 to 20 carbon atoms), an alkoxy group (e.g., containing 1 to 20 carbon atoms), an aryloxy group (e.g., phenoxy, naphthoxy, substituted phenoxy containing a substituent having 1 to 14 carbon atoms, substituted naphthoxy containing a substituent having 1 to 10 carbon atoms), an acylamino group (e.g., in which the acyl moiety has 1 to 20 carbon atoms), an alkylsulfonamido group (e.g., having 1 to 20 carbon atoms), an arylsulfonamido group (e.g., phenylsulfonamido, naphthylsulfonamido, substituted phenylsulfonamido in which the substituent has from 1 to 14 carbon atoms, substituted naphthylsulfonamido in which the substituent has from 1 to 10 carbon atoms), an alkylamino group (e.g., having 1 to 20 carbon atoms), an arylamino group (e.g., phenylamino, naphthylamino, substituted phenylamino having a substituent containing 1 to 14 carbon atoms, substituted naphthylamino having a substituent containing 1 to 10 carbon atoms), etc. $R_3$ and $R_4$ can also fuse to form an aliphatic ring, an aromatic ring, a heterocyclic ring, more specifically to form, a cyclopentane, cyclohexane, cycloheptane, benzene, and substituted benzene ring which is substituted with a halogen atom, an amino group, a hydroxy group, a sulfo group, a carboxy group, a sulfonamido group, or an alkyl, alkoxy, acylamino, alkylamino, or arylamino group, each as above defined or a pyridine ring a dihydrofuran ring, dihydrothiophene ring, theophene ring (especially, 5 to 6 membered ring).

Specific examples of compounds having a pyridine ring, are e.g., pyridine, α-picoline, γ-picoline, 3-butylpyridine, 4-propylpyridine, 3-amylpyridine, 3-benzylpyridine, 4-β-phenylethylpyridine, 4-β-(4-methoxyphenyl)ethylpyridine, 4-β-(4-hydroxy-3-methoxyphenyl)ethylpyridine, 3,5-lutidine, 3-ethyl-4-methylpyridine, 3-methylquinoline, 3,4-dimethylquinoline, 7-chloro-3-methylquinoline, 2,4,6-trimethylquinoline, 1,2-bis-(4-pyridyl)-ethane, 4-bromo-pyridine, 4-(p-chlorobenzyl)-pyridine, 2,3,6-collidine, 3,4-lutidine, 3,5-dichloropyridine, 4,4'-dipyridyl, 4-phenylpyridine, isoquinoline, phenanthridine, 4-methanolpyridine, 3-acetylaminopyridine, and the like.

Some specific examples of ylide compounds obtained as a starting material in the present invention are described below.

Compound 1-1

1-(2,4,6-Trichlorophenyl)-3-[3-{(2,4-di-tert-amylphenoxy)-acetamido}benzamido]-4-(1-pyridinio)-5-oxo-2-pyrazolin-4-ide Compound 1-2

1-(2,4,6-Trichlorophenyl)-3-[3-{α-(2,4-di-tert-amylphenoxy)-butyramido}benzamido]-4-(1-pyridinio)-5-oxo-2-pyrazoline bromide Compound 1-3

1-(2,4,6-Trichlorophenyl)-3-[3-{(2,4-di-tert-amylphenoxy)-acetamido}benzamido]-4-(3-ethyl-4-methyl-1-pyridinio)-5-oxo-2-pyrazolin-4-ide Compound 1-4

1-(2,6-Dichloro-4-methoxyphenyl)-3-[3-{(2,4-di-tert-amylphenoxy)-acetamido}benzamido]-4-(1-pyridinio)-5-oxo-2-pyrazolin-4-ide Compound 1-5

1-(2,6-Dichloro-4-methylphenyl)-3-[{α-(2,4-di-tert-amylphenoxy)}-butyramido]-4-(1-pyridinio)-5-oxo-2-pyrazoline bromide Compound 1-6

1-(2,6-Dichloro-4-methoxyphenyl)-3-[3-{α-(2,4-di-tert-amylphenoxy)-butyramido}phenylureido]-4-(1-pyridinio)-5-oxo-2-pyrazolin-4-ide Compound 1-7

1-(2,4,6-Trichlorophenyl)-3-n-butyloxy-4-(2-isoquinolinio-5-oxo-2-pyrazolin-4-ide Compound 1-8

1-(2,4,6-Trichlorophenyl)-3-(2-chloro-5-dodecyloxycarbonylanilino)-4-(1-pyridinio)-5-oxo-2-pyrazolin-4-ide Compound 1-9

1-Phenyl-3-methyl-4-(1-pyridinio)-5-oxo-2-pyrazolin-4-ide

Compound 1-10

1-(2,4,6-Trichlorophenyl)-3-[2-chloro-5-{α-(2,4-di-tert-amylphenoxy)butyramido}anilino]-4-(1-pyridino)-5-oxo-2-pyrazoline iodide Compound 1-11

1-(4-Acetamidophenyl)-3-ethoxy-4-(3-ethyl-4-methyl-1-pyridinio)-5-oxo-2-pyrazolin-4-ide Compound 1-12

1-(2,4,6-Trichlorophenyl)-3-[3-{α-(2,4-di-tert-amylphenoxy)-butyramido}benzamido]-4-(2-isoquinolinio)-5-oxo-2-pyrazoline bromide Compound 1-13

1-(2-Chloro-4,6-dimethylphenyl)-3-[3-{γ-(3-pentadecylphenoxy)-butyramido}benzamido]-4-(1-pyridinio)-5-oxo-2-pyrazolin-4-ide Compound 1-14

1-(2,4,6-Trichlorophenyl)-3-cyclohexylamino-4-(1-pyridinio)-5-oxo-2-pyrazoline iodide Compound 1-15

1-[4-{α-(3-n-Pentadecylphenoxy)butyramido}-phenyl]-3-benzamido-4-(1-pyridinio)-5-oxo-2-pyrazolin-4-ide Compound 1-16

1-Phenyl-3-(3-n-tetradecanamido)anilino-4-(4-propylpyridinio)-5-oxo-2-pyrazolin-4-ide Compound 1-17

1-(2,4,6-Trichlorophenyl)-3-(4-n-tetradecanamido)anilino-4-(3,5-dimethyl-1-pyridinio)-5-oxo-2-pyrazolin-4-ide Compound 1-18

1-(2,4,6-Trichlorophenyl)-3-[2-chloro-5-(n-tetradecanamido)anilino]-4-(1-pyridinio)-5-oxo-2-pyrazolin-4-ide The above-illustrated ylide compounds can be converted to the corresponding 4-substituted piperidino-5-oxo-2-pyrazolines with ease in high yield using a catalytic reduction in the presence of a metal hydrogenation catalyst in a suitable solvent at atmospheric pressures or under an applied pressure.

As the solvent, any of the alcohols, esters, organic acids (e.g., acetic acid, etc.) and aprotic polar solvents such as dimethylformamide, dimethylacetamide, N-methylpyrrolidone, dimethylsulfoxide and the like can be used as long as the ylide compounds are soluble in the solvent employed. Preferred solvents are acetic acid, methanol, dimethylformamide, etc. These solvents are usually employed in an amount of about 50 to about 500 ml, preferably, about 50 to about 200 ml, to about 10 g of the ylide compounds.

As the reducing catalyst, conventionally employed metal catalysts such as platinum oxide, a catalyst of the palladium series and the nickel series are effective. Specific examples of suitable metal catalysts include Raney-Ni, 10% palladium-carbon, etc. The preferred amount of the metal catalysts used is from about 0.1 to about 50 g, preferably about 0.5 to 20 g, to about 10 g of the ylide compound. Generally palladium-system catalysts are supported, and the reaction mixture contacted therewith and nickel-system catalysts are suspended in the reaction mixture. Of them, a Raney nickel catalyst is particularly effective.

A suitable reaction temperature can range from about 20° to 150° C, preferably from 20° C to 80° C.

The reaction time can be shortened by increasing the reaction temperature to above 50° C, preferably above 70° C. When volatile solvents such as methanol or ethanol are employed, after filtering off the catalyst, the solvents are removed under reduced pressure. The residue is crystallized from suitable solvents. In case of using non-volatile solvents such as acetic acid, dimethylformamide, etc., after removing the catalyst by filtration, the filtrate is poured into a large amount, e.g., 10 times (by volume), of ice-water to crystallize out the solids. The solids are filtered, dried and recrystallized from suitable solvents.

Some specific examples of 1,3-di-substituted-4-substituted piperidino-5-oxo-2-pyrazolines, produced from the above-illustrated ylide compounds, are described below. However, the present invention is not to be interpreted as being limited only to these examples.

Compound 2-1

1-(2,4,6-Trichlorophenyl)-3-[3-{(2,4-di-tert-amylphenoxy)-acetamido}benzamido]-4-piperidino-5-oxo-2-pyrazoline Compound 2-2

1-(2,4,6-Trichlorophenyl)-3-[3-{α-(2,4-di-tert-amylphenoxy)butyramido}benzamido]-4-piperidino-5-oxo-2-pyrazoline Compound 2-3

1-(2,4,6-Trichlorophenyl)-3-[3-{(2,4-di-tert-amylphenoxy)acetamido}benzamido]-4-(3-ethyl-4-methyl-piperidino)-5-oxo-2-pyrazoline Compound 2-4

1-(2,6-Dichloro-4-methoxyphenyl)-3-[3-{(2,4di-tert-amylphenoxy)-acetamido}benzamido]-4-piperidino-5-oxo-2-pyrazoline Compound 2-5

1-(2,6-Dichloro-4-methylphenyl)-3-[α-(2,4-di-tert-amylphenoxy)]-butyramido-4-piperidino-5-oxo-2-pyrazoline Compound 2-6

1-)2,6-Dichloro-4-methoxyphenyl)-3-[3-{α-(2,4-di-tert-amylphenoxy)-butyramido}phenylureido]-4-piperidino-5-oxo-2-pyrazoline Compound 2-7

1-(2,4,6-Trichlorophenyl)-3-n-butyloxy-4-N-(1,2,3,4-tetrahydroisoquinolyl)-5-oxo-2-pyrazoline Compound 2-8

1-(2,4,6-Trichlorophenyl)-3-(2chloro-5-dodecanoxycarbonylanilino)-4-piperidino-5-oxo-2-pyrazoline Compound 2-9

1-Phenyl-3-methyl-4-piperidino-5-oxo-pyrazoline

Compound 2-10

1-(2,4,6-Trichlorophenyl)-3-[2-chloro-5-{α-(2,4-di-tert-amylphenoxy)butyramido}anilino]-4-piperidino-5-oxo-2-pyrazoline Compound 2-11

1-(4-Acetamidophenyl)-3-ethoxy-4-(3thyl-4-methyl-piperidino)-5-oxo-2-pyrazoline

Compound 2-12

1-(2,4,6-Trichlorophenyl)-3-[3-{α-(2,4-di-tert-amylphenoxy)- butyramido}benzamido]-4-N-(1,2,3,4tetrahydroisoquinolyl)-5-oxo-2-pyrazoline Compound 2-13

1-(2-Chloro-4,6-dimethylphenyl)-3-(3-{γ-(3-pentadecylphenoxy)-butyramido}benzamido]-4-piperidino-5-oxo-2-pyrazoline Compound 2-14

1-(2,4,6-Trichlorophenyl)-3-cyclohexyl-4-piperidino-5-oxo-2-pyrazoline

Compound 2-15

1-[4-{α-(3-n-Pentadecanylphenoxy)butyramido}-phenyl]-3-benzamido-4-N-piperidino-5-oxo-2-pyrazoline Compound 2-16

1-Phenyl-3-(3-tetradecanamido)anilino-4-(4-n-propylpiperidino) 5-oxo-2-pyrazoline Compound 2-17

1-(2,4,6-Trichlorophenyl)-3-(4-n-tetradecanamido)anilino--(3,5-dimethylpiperidino)-5-oxo-2-pyrazoline Compound 2-18

1-(2,4,6-Trichlorophenyl)-3-[2-chloro-5-(n-tetradecanamido)anilino]-4-piperidino-5-oxo-2-pyrazoline The present invention will now be illustrated in greater detail by reference to the following examples which, however, are not intended to be interpreted as limiting the present invention in any way. Unless otherwise indicated herein, all parts, percents, ratios and the like are by weight.

EXAMPLE 1

Production of 1-(2,4,6-Trichlorophenyl)-3-[3-{2,4-di-tert-amylphenoxy)acetamido} benzamido]-4-piperidino-5-oxo-2-pyrazoline (Compound 2-1)

15 Grams of 1-(2,4,6-trichlorophenyl)-3-[3-{(2,4-di-tert-amylphenoxy)acetamido} benzamido]-4-(1-pyridino)-5-oxo-2-pyrazolin-4-ide . (Compound 1-1; m.p.: 178°–180° C) was dissolved in 200 ml of acetic acid, with about 20 g of freshly prepared Raney nickel being added thereto. Then, the system was heated to 60°–80° C and stirred for 30 hours in a stream of hydrogen. After confirming by this layer chromatography that the starting material was consumed, the catalyst was filtered off, and the mother liquor was concentrated. Upon recrystallizing the resulting concentrate from an acetonitrile-ethyl acetate mixed solvent (10:1, by volume), 11.5 g of Compound 2-1 having a melting point of 218° C was obtained.

Elemental Analysis

Calcd. for $C_{39}H_{46}N_5O_4Cl_3$: C (62.1%); H (6.10%); N (9.29% ; Found: C (61.96%); H (6.04%); N (9.24%.

IR (Nujol mull)

1710 $cm^{-1}$, 1633 $cm^{-1}$ and 1612 $cm^{-1}$

EXAMPLE 2

Production of 1-(2,4,6-Trichlorophenyl)-3-[3-{α-(2,4-di-tert-amylphenoxy)butyramido} benzamido]-4-piperidino-5-oxo-2-pyrazoline (Compound 2-2):

15 Grams of 1-(2,4,6-trichlorophenyl)-3-[3-{α-(2,4-di-tert-amylphenoxy)butyramido} benzamido]-4-(1-pyridinio)-5-oxo-2-pyrazoline bromide (Compound 1-2; m.p: 260° - 262° C) was dissolved in 300 ml of acetic acid, with 10 g of Raney nickel being added thereto. The resulting mixture was maintained at 80° C and vigorously stirred for 24 hours in a stream of hydrogen. Then, the reaction product was treated in the same manner as described in Example 1. Upon recrystallizing from a chloroform-ethyl acetateacetonitrile mixed solvent (1:1:10 by volume), 8.5 g of Compound 2-2 having a melting point of 186°–190° C was obtained.

Elemental Analysis

Calcd. for $C_{41}H_{50}N_5O_4Cl_3$: C (62.9%; H (6.40%); N (8.95%). Found: C (63.10%); H (6.41%; N (8.93%).

IR (Nujol mull)

1740 $cm^{-1}$, 1720 $cm^{-1}$, 1690 $cm^{-1}$, 1635 $cm^{-1}$, 1615 $cm^{-1}$, 1588 $cm^{-1}$

EXAMPLE 3

Production of 1-(2,4,6-Trichlorophenyl)-3-[3-{(2,4-di-tert-amylphenoxy)acetamido} benzamido]-4-(3-ethyl-4-methylpiperidino)-5-oxo-2-pyrazoline (Compound 2-3)

7.9 grams of 1-(2,4,6-trichlorophenyl)-3-[3-{(2,4-di-tert-amylphenoxy)acetamido} benzamido]-4-(3-ethyl-4-methyl-1-pyridinio)-5-oxo-2-pyrazolin-4-ide (Compound 1-3; m.p.; 162° - 165° C) was dissolved in 500 ml of ethanol, and about 10 g of Raney nickel catalyst was added thereto. Then, reaction was conducted in an autoclave at 80° C for 20 hours with an initial hydrogen pressure of 60 atmospheres. After the reaction, the catalyst was removed, followed by distilling off the solvent. Upon crystallizing the resulting residue from acetonitrile-ethyl acetate (10:1 by volume) 4.2 g of Compound 2-3 having a melting point of 145° - 155° C was obtained.

Elemental Analysis

Calcd. for $C_{42}H_{52}N_5O_4Cl_3$: C (63.3%); H (6.53%); N (8.79%). Found C (63.1%); H (6.54%); N (8.80%.

IR (Nujol mull)

1715 $cm^{-1}$, 1641 $cm^{-1}$, 1615 $cm^{-1}$

EXAMPLE 4

Production of 1-(2,4,6-Trichlorophenyl)-3-[3-{α-(2,4-di-tert-amylphenoxy)} butyamido]-4-N-(1,2,3,4-tetrahydroisoquinolyl)-5-oxo-2-pyrazoline (Compound 2-12): 6 Grams of 1-(2,4,6-trichlorophenyl)-3-[3-{α-(2,4-di-tert-amylphenoxy)butyramido} benzamido]-4-(2-isoquinolinio)-5-oxo:2-pyrazoline bromide (Compound 1-12; m.p.: 185° - 185° C) was dissolved in 300 ml of ethanol with 3 g of 10% palladium-carbon catalyst. Then, reaction was conducted in an autoclave at 70° C for 12 hours with an initial hydrogen pressure of 60 atmospheres. After the completion of the reaction, the catalyst was filtered off, followed by distilling off the solvent under reduced pressure. Upon immediately recrystallizing the residue from acetonitrileethyl acetate (10:1 by volume), 3.5 g of Compound 2-12 having a melting point of 150° - 153° C was obtained.

Elemental Analysis

Calcd. for $C_{45}H_{50}N_5O_4Cl_3$: C (65.0%); H (6.02%); N (8.42%). Found: C (65.1%); H (6.10%; N (8.40%).

IR (Nujol mull) 1715 $cm^{-1}$, 1640 $cm^{-1}$, 1616 $cm^{-1}$

EXAMPLE 5

Production of 1-(2,4,6-Trichlorophenyl)-3-[2-chloro-5-(n-tetradecanamido)anilino]-4-piperidino-5-oxo-2-pyrazoline (Compound 2-18):

2.0 Grams of 1-(2,4,6-trichlorophenyl)-3-[2-chloro-5-(n-tetra-decanamido)anilino]-4-(1-pyridinio)-5-oxo-2-pyrazoline-4-ide Compound 1-18; m.p/: 124°–128° C) was hydrogenated in the same manner as described in Example 3 using a Raney nickel catalyst (1 g, wet weight), and was treated in the same manner. Upon recrystallizing from hexane-ethyl acetate (10:1, by volume), 1.2 g of Compound 2-18 having a melting point of 148° - 153° C was obtained.

Elemental Analysis

Calcd. for $C_{34}H_{45}N_5O_2Cl_4$: C (58.5%); H (6.46%); N (10.0%). Found: C (58.3%); H (6.50%); N (9.98%).

IR (Nujol mull)

1720 $cm^{-1}$, 1705 $cm^{-1}$, 1610 $cm^{-1}$

While the invention has been described in detail and with reference to specific embodiments thereof, it will be apparent to one skilled in the art that various changes and modifications can be made therein without departing from the spirit and scope thereof.

What is claimed is:

1. A compound of the formula (X):

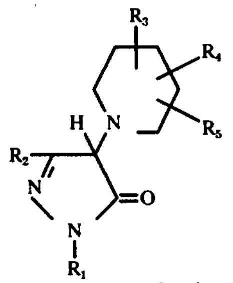

wherein $R_1$ represents a group having from about 6 to about 40 carbon atoms chosen from the group consisting of phenyl substituted with one or more of the following; alkly groups having 1 to 30 carbon atoms, alkoxy having 1 to 30 carbon atoms, phenyl, naphthyl, phenoxy, naphthoxy, phenoxy or napthoxy substituted with a group having 1 to 10 carbon atoms, halogen, alkoxycarbonyl having 1 to 30 carbon atoms, acylamino having 1 to 30 carbon atoms, carbamoyl having 1 to 30 carbon atoms, sulfo, alkylsulfonamido having 1 to 30 carbon atoms; phenylsulfonamido, naphthylsulfonamido, phenyl- or naphthylsulfonamido having a substituent having 1 to 20 carbon atoms, sulfamoyl having 1 to 30 carbon atoms or a carboxy group; $R_2$ represents hydrogen, halogen, amino, hydroxy, sulfo, alkyl having 1 to 45 carbon atoms, phenyl, naphthyl, phenyl or naphthyl substituted with a substituent having 1 to 30 carbon atoms, alkoxy having 1 to 45 carbon atoms, cycloalkylamino having 3 to 8 carbon atoms with a substituent containing 1 to 30 carbon atoms, dialkylamino in which each alkyl has 1 to 20 carbon atoms, diphenylamino or dinaphthylamino having a substituent with 1 to 15 carbon atoms, arylamino wherein the moiety has 6 to 45 carbon atoms, acylamino wherein the acyl moiety has 1 to 45 carbon atoms, N-alkylacylamino in which the acyl moiety has 1 to 30 carbon atoms and in which the alkyl moiety has 1 to 10 carbon atoms, carbamoyl having 1 to 45 carbon atoms, phenylacylamino or naphthylacylamino, in which the acyl moiety has 1 to 20 carbon atoms, phenylacylamino in which the acyl moiety has 1 to 20 carbon atoms and having a substituent having 1 to 10 carbon atoms, ureido, N-alkylureido, N-phenylureido, N-naphthylureido having 1 to 45 carbon atoms, N-substituted phenylureido and N-substituted naphthylureido having 1 to 20 carbon atoms in the substituent group, N-cycloalkylureido having 1 to 20 carbon atoms, and diacylamino in which the acyl substituent has 1 to 20 carbon atoms; $R_3$, $R_4$ and $R_5$ each represent hydrogen, hydroxy, halogen, amide, sulfoalkyl havng 1 to 20 carbon atoms, aralkyl having 1 to 20 carbon atoms, alkoxy having 1 to 20 carbon atoms, phenoxy, naphthoxy, phenoxy having a substituent having 1 to 14 carbon atoms, naphthoxy with a substituent having 1 to 10 carbon atoms, acylamino in which the acyl moeity has 1 to 20 carbon atoms, alkylsulfonamido having 1 to 20 carbon atoms, phenylsulfonamido having 1 to 20 carbon atoms, phenylsulfonamido, naphthylsulfonamido, phenylsulfornamido having a substituent having 1 to 14 carbon atoms, naphthylsulfonamido having a substituent having 1 to 10 carbon atoms, alkylamino having 1 to 20 carbon atoms, phenylamino, naphthylamino, phenylamino having a substituent having 1 to 14 carbon atoms, and $R_3$ and $R_4$ can combine together to represent cyclopentane, cyclohexane, cycloheptane, benzene, benzene substituted with halogen, amino, hydroxy, sulfo, carboxy, sulfonamido, alkyl, alkoxy, acylamino, alkylamino, arylamino, pyridine, dihydrofuran, dihydrothiophene or thiophene.

2. A 4-piperidino-5-oxo-2-pyrazoline as described in claim 1, wherein $R_1$ represents a phenyl group or a phenyl group having at least three substitutents selected from the group consisting of a halogen atom, an alkyl group and an alkoxy group, $R_2$ represents an alkyl group, a hydroxy group, an amino group a carboxamido group, or a phenylamino group, and $R_3$, $R_4$ and $R_5$ each represents a hydrogen atom, an alkyl group, or a halogen atom.

3. The compound 1-(2,4,6-trichlorophenyl)-3-[3-{(2,4-di-tert-amylphenoxy)-acetamido}-benzamido]-4-piperidino-5-oxo-2-pyrazoline.

4. The compound 1-(2,4,6-trichlorophenyl)-3-[3-{α-(2,4-di-tert-amylphenoxy)-butyramido}benzamido]-4-piperidino-5-oxo-2-pyrazoline.

5. The compound 1-(2,4,6-trichlorophenyl)-3-[3-{(2,4-di-tert-amylphenoxy)acetamido}benzamido]-4-(3-ethyl-4-methyl-piperidino)-5-oxo-2-pyrazoline.

6. The compound 1-(2,4,6-trichlorophenyl)-3-[2-chloro-5-(n-tetradecanamido)-anilino]-4-piperidino-5-oxo-2-pyrazoline.

7. A piperidino-5-oxo-2-pyrazoline as described in claim 1, wherein $R_2$ represents a non-carbon containing substitutent group selected from a hydroxy, amino, or sulfo group.

8. A 4-piperidino-5-oxo-2-pyrzaoline as described in claim 1, wherein $R_3$, $R_4$ and $R_5$ represents a non-carbon containing substituent group selected from a hydroxy, amino, or sulfo group.

* * * * *